United States Patent
Hong et al.

(10) Patent No.: US 8,241,354 B2
(45) Date of Patent: Aug. 14, 2012

(54) EXTENDED DEPTH OF FOCUS (EDOF) LENS TO INCREASE PSEUDO-ACCOMMODATION BY UTILIZING PUPIL DYNAMICS

(75) Inventors: Xin Hong, Fort Worth, TX (US); Mutlu Karakelle, Fort Worth, TX (US); Xiaoxiao Zhang, Fort Worth, TX (US); Michael Simpson, Arlington, TX (US); Myoung Choi, Arlington, TX (US); Yan Zhang, Vernon, CT (US)

(73) Assignee: Novartis AG, Basel (CH)

( * ) Notice: Subject to any disclaimer, the term of this patent is extended or adjusted under 35 U.S.C. 154(b) by 206 days.

(21) Appl. No.: 12/503,267

(22) Filed: Jul. 15, 2009

(65) Prior Publication Data

US 2010/0016961 A1   Jan. 21, 2010

Related U.S. Application Data

(60) Provisional application No. 61/080,790, filed on Jul. 15, 2008.

(51) Int. Cl.
   *A61F 2/16* (2006.01)
(52) U.S. Cl. ........................ 623/6.27; 623/6.28; 623/6.29
(58) Field of Classification Search .................. 623/6.24, 623/6.27–6.3
   See application file for complete search history.

(56) References Cited

U.S. PATENT DOCUMENTS

| | | | |
|---|---|---|---|
| 7,188,949 B2 * | 3/2007 | Bandhauer et al. ........... 351/168 |
| 7,381,221 B2 * | 6/2008 | Lang et al. .................. 623/6.24 |
| 2006/0244904 A1 * | 11/2006 | Hong et al. ............... 351/160 R |
| 2007/0129800 A1 | 6/2007 | Cumming | |
| 2007/0236769 A1 | 10/2007 | Zalevsky | |

FOREIGN PATENT DOCUMENTS

| | | | |
|---|---|---|---|
| EP | 0367 878 | * | 5/1990 |
| WO | 03009053 A | | 1/2003 |
| WO | 2007067872 A | | 6/2007 |
| WO | 2008083283 A | | 7/2008 |

OTHER PUBLICATIONS

International Search Report for PCT/US2009/050731, Publication No. WO2010/009254, 4 pages.
Written Opinion of the International Searching Authority, International Application No. PCT/US2009/050731, 6 pages.

(Continued)

*Primary Examiner* — David H Willse
*Assistant Examiner* — Tiffany Shipmon
(74) *Attorney, Agent, or Firm* — Jonathan E. Prejean

(57) ABSTRACT

In one aspect, the present invention provides an ophthalmic lens (e.g., an IOL) that includes an optic having an anterior surface and a posterior surface disposed about an optical axis. At least one of the surfaces (e.g., the anterior surface) has a profile characterized by superposition of a base profile and an auxiliary profile. The auxiliary profile can include an inner region, an outer region and a transition region between the inner and the outer regions, where an optical path difference across the transition region (i.e., the optical path difference between the inner and the outer radial boundaries of the transition region) corresponds to a non-integer fraction (e.g., ½) of a design wavelength (e.g., a wavelength of about 550 nm).

14 Claims, 9 Drawing Sheets

OTHER PUBLICATIONS

PCT International Preliminary Report on Patentability, PCT/US2009/050731, Jan. 18, 2011, 7 pages.

International Search Report for PCT/US2009/050731, Filed Jul. 15, 2009; Publication No. WO2010/009254, Published Jan. 21, 2010, 4 pages.

Written Opinion of the International Searching Authority; International Application No. PCT/US2009/050731, Filed Jul. 15, 2009; 6 pages.

PCT International Preliminary Report on Patentability, PCT/US2009/050731, Filed Jul. 15, 2009, 7 pages.

* cited by examiner

D2 = 1μm

Advanced Wavefront

D2 = -1μm

Delayed Wavefront

Zsag = Zbase + Zaux =

EXTENDED DEPTH OF FOCUS (EDOF) LENS TO INCREASE PSEUDO-ACCOMMODATION BY UTILIZING PUPIL DYNAMICS

This application claims priority to U.S. Patent Application Ser. No. 61/080,790 filed on Jul. 15, 2008.

RELATED APPLICATION

The present invention is related to U.S. patent application entitled "Accommodative IOL with Toric Optic and Extended Depth of Focus," which is concurrently filed herewith. This application is herein incorporated by reference.

BACKGROUND

The present invention relates generally to ophthalmic lenses, and more particularly, to intraocular lenses (IOLs) that provide enhanced vision via controlled variation of the phase shift across a transition region provided on at least one of the lens surfaces.

Intraocular lenses (IOLs) are routinely implanted in patients' eyes during cataract surgery to replace the natural crystalline lens. The optical power of the natural crystalline lens can vary under the influence of the ciliary muscles to provide accommodation for viewing objects at different distances from the eye. Many IOLs, however, provide a monofocal power with no provision for accommodation. Multifocal IOLs are also known that provide a distance optical power as well as a near optical power (e.g., by employing diffractive structures), thereby providing a degree of pseudoaccommodation.

There is, however, still a need for improved IOLs that can provide pseudo-accommodative optical power while providing sharp optical images over a wide range of pupil sizes. In designing IOLs and lenses generally, optical performance can be determined by measurements using a so-called "model eye" or by calculations, such as predictive ray tracing. Typically, such measurements and calculations are performed based on light from a narrow selected region of the visible spectrum to minimize chromatic aberrations. This narrow region is known as the "design wavelength."

SUMMARY

In one aspect, the present invention provides an ophthalmic lens (e.g., an IOL) that includes an optic having an anterior surface and a posterior surface disposed about an optical axis. At least one of the surfaces (e.g., the anterior surface) has a profile characterized by superposition of a base profile and an auxiliary profile. The auxiliary profile can include at least two regions (e.g., an inner region and an outer region) and one or more transition regions between the regions, where an optical path difference across the transition region (i.e., the optical path difference between the inner and the outer radial boundaries of the transition region) corresponds to a non-integer fraction (e.g., ½) of a design wavelength (e.g., a wavelength of about 550 nm).

The transition region of the auxiliary profile can extend from an inner radial boundary to an outer radial boundary. In many embodiments, the inner radial boundary of the transition region corresponds to an outer radial boundary of the inner region and the outer radial boundary of the transition region correspond to an inner radial boundary of the outer region of the auxiliary profile. In many embodiments, the transition region can be adapted to provide a monotonic change in optical path difference relative to its inner radial boundary as a function of increasing radial distance from the optical axis. A monotonic change in the optical path difference can be characterized by a continuous increase or decrease as a function of radial distance, which in some cases is interspersed with regions of no change (plateau regions). By way of example, the monotonic change can be characterized by a linear change or by a succession of linear changes separated by one or more plateaus.

In some embodiments, the profile ($Z_{sag}$) of the surface formed as superposition of a base profile and an auxiliary profile can be defined by the following relation:

$$Z_{sag} = Z_{base} + Z_{aux},$$

wherein, $Z_{sag}$ denotes a sag of the surface relative to the optical axis as a function of radial distance from that axis, and wherein, $$z_{base} = \frac{cr^2}{1 + \sqrt{1 - (1+k)c^2 r^2}} + a_2 r^2 + a_4 r^4 + a_6 r^6 + \ldots,$$

wherein, r denotes a radial distance from the optical axis, c denotes a base curvature of the surface, k denotes a conic constant, $a_2$ is a second order deformation constant, $a_4$ is a fourth order deformation constant, $a_6$ is a sixth order deformation constant, and wherein, $$Z_{aux} = \begin{cases} 0, & 0 \leq r < r_1 \\ \frac{\Delta}{(r_2 - r_1)}(r - r_1), & r_1 \leq r < r_2 \\ \Delta, & r_2 < r \end{cases}$$

wherein, $r_1$ denotes an inner radial boundary of the transition region, $r_2$ denotes an outer radial boundary of the transition region, and wherein, Δ is defined by the following relation:

$$\Delta = \frac{\alpha \lambda}{(n_2 - n_1)},$$

wherein, $n_1$ denotes an index of refraction of material forming the optic, $n_2$ denotes an index of refraction of a medium surrounding the optic, λ denotes a design wavelength (e.g., 550 nm), and α denotes a non-integer fraction (e.g., ½).

In some other embodiments, the profile ($Z_{sag}$) of the lens surface having the auxiliary profile can be defined by the following relation:

$$Z_{sag} = Z_{base} + Z_{aux}$$

wherein, $Z_{sag}$ denotes a sag of the surface relative to the optical axis as a function of radial distance from that axis, and wherein, $$z_{base} = \frac{cr^2}{1+\sqrt{1-(1+k)c^2r^2}} + a_2r^2 + a_4r^4 + a_6r^6 + \dots,$$

wherein, r denotes a radial distance from the optical axis,
c denotes a base curvature of the surface,
k denotes a conic constant,
$a_2$ is a second order deformation constant,
$a_4$ is a fourth order deformation constant,
$a_6$ is a sixth order deformation constant, and wherein, $$z_{aux} = \begin{cases} 0, & 0 \le r < r_{1a} \\ \frac{\Delta_1}{(r_{1b}-r_{1a})}(r-r_{1a}), & r_{1a} \le r < r_{1b} \\ \Delta_1, & r_{1b} \le r < r_{2a} \\ \Delta_1 + \frac{(\Delta_2-\Delta_1)}{(r_{2b}-r_{2a})}(r-r_{2a}), & r_{2a} \le r < r_{2b} \\ \Delta_2 & r_{2b} < r \end{cases}$$

wherein r denotes the radial distance from an optical axis of the lens,
$r_{1a}$ denotes the inner radius of a first substantially linear portion of transition region of the auxiliary profile,
$r_{1b}$ denotes the outer radius of the first linear portion,
$r_{2a}$ denotes the inner radius of a second substantially linear portion of the transition region of the auxiliary profile, and
$r_{2b}$ denotes the outer radius of the second linear portion, and wherein each of $\Delta_1$ and $\Delta_2$ can be defined in accordance with the following relation:

$$\Delta_1 = \frac{\alpha_1 \lambda}{(n_2-n_1)}, \text{ and}$$

$$\Delta_2 = \frac{\alpha_2 \lambda}{(n_2-n_1)}, \text{ and}$$

wherein, $n_1$ denotes an index of refraction of material forming the optic,
$n_2$ denotes an index of refraction of a medium surrounding the optic,
$\lambda$ denotes a design wavelength (e.g., 550 nm),
$\alpha_1$ denotes a non-integer fraction (e.g., ½), and
$\alpha_2$ denotes a non-integer fraction (e.g., ½).

By way of example, in the above relations, the base curvature c can be in a range of about 0.0152 mm$^{-1}$ to about 0.0659 mm$^{-1}$, and the conic constant k can be in a range of about −1162 to about −19, $a_2$ can be in a range of about −0.00032 mm$^{-1}$ to about 0.0 mm$^{-1}$, $a_4$ can be in a range of about 0.0 mm$^{-3}$ to about −0.000053 (minus 5.3×10$^{-5}$) mm$^{-3}$, and $a_6$ can be in a range of about 0.0 mm$^{-5}$ to about 0.000153 (1.53× 10$^{-4}$) mm$^{-5}$.

In another aspect, an ophthalmic lens (e.g., an IOL) is disclosed that includes an optic having an anterior surface and a posterior surface disposed about an optical axis. At least one of those surfaces includes at least one inner refractive region, at least one outer refractive region, and a refractive transition region that extends from an outer radial boundary of the inner region to an inner radial boundary of the outer region. The transition region is adapted such that a phase of radiation incident thereon at a design wavelength (e.g., 550 nm) varies monotonically from said inner radial boundary to said outer radial boundary so as to generate a phase shift between those boundaries that is characterized by a non-integer fraction of that design wavelength. While in some cases the non-integer fraction is less than one, in other cases it is greater than one.

In some embodiments, the anterior and the posterior surfaces exhibit base profiles adapted to impart a nominal refractive optical power, e.g., a power in a range of about −15 to about +50 Diopters, to the lens.

In a related aspect, the surface having the transition region can have a radial diameter in a range of about 1 mm to about 5 mm, and the transition region can be in the form of an annular region having a radial width in a range of about 0 to about 1 mm.

In another aspect, in the above ophthalmic lens, the optic exhibits a through-focus modulation transfer function that is asymmetric relative to a focal plane of the optic for aperture sizes in a range of about 1.5 mm to about 6 mm.

In another aspect, an ophthalmic lens (e.g., an IOL) is disclosed that includes an optic having an anterior surface and a posterior surface disposed about an optical axis, where each surface includes a base surface profile. A pattern of surface variations are superimposed on the base surface profile of at least one of the surfaces so as to generate a transition region extending between an inner and an outer surface region. The transition region causes the optic to exhibit an asymmetric through-focus modulation transfer function of light incident on the optic (e.g., light having a design wavelength (e.g., 550 nm)) through an aperture having a diameter in a range of about 1.5 mm to about 6 mm.

In some embodiments, the above lens can exhibit a depth of field in a range of about 0.25 Diopters to about 1.75 Diopters for light incident thereon through an aperture having a diameter in a range of about 1.5 mm to about 6 mm for said design wavelength.

In some embodiments, the above lens can exhibit a substantially symmetric through-focus modulation transfer function for light at the design wavelength incident on the optic through an aperture having a diameter less than about 2 mm while exhibiting an asymmetric through-focus modulation transfer function for greater apertures. In some cases, the optic exhibits a depth-of-field in a range of about 0.25 D to about 1.75 D for light incident thereon through an aperture having a diameter in a range of about 1.5 mm to about 6 mm for the design wavelength.

In another aspect, the invention provides an ophthalmic lens (e.g., an IOL), which comprises an optic having an anterior surface and a posterior surface, where each surface has a base profile such that the profiles cooperatively impart a nominal optical power to the optic. At least one of the surfaces has a profile defined by addition of an auxiliary surface profile to its nominal surface profile, where the auxiliary profile is characterized by a central region, an outer region and a transition region extending between the inner and the outer regions. The auxiliary profile is adapted to cause a shift between an effective optical power and said nominal optical power for light having a design wavelength and incident on the optic through an aperture having a size in a selected range, e.g., a shift in a range of about 0.25 D to about 1.75 D. The effective optical power can be characterized by the peak of a through-focus modulation transfer function of the optic at said design wavelength and said aperture.

In a related aspect, in the above lens, the auxiliary profile is adapted to enhance the depth of field of the optic.

In another aspect, an ophthalmic lens (e.g., an IOL), is disclosed that includes an optic having an anterior surface and a posterior surface disposed about an optical axis. At least one of the surfaces includes at least an inner refractive region and at least an outer refractive region, where the profile of that surface is configured to impart a monotonically changing phase shift to incident radiation (e.g., incident radiation at a design wavelength) from an outer boundary of the inner region to an inner boundary of the outer region to provide a phase shift between the two boundaries that is a non-integer fraction of a design wavelength (e.g., 550 nm). In some cases, the surface profile is configured such that the phase shift would occur over a radial distance in a range of about 0.75 mm to about 2.5 mm. Further, in some cases, the phase shift can effect an extension of the depth-of-focus exhibited by the optic by a value in a range of about 0.25 D to about 1.75 D.

In a related aspect, the radial derivative of the profile of that surface at the outer boundary of the inner region exhibits a discontinuity.

Further understanding of the invention can be obtained by reference to the following detailed description and the accompanying drawings, which are described briefly below.

DETAILED DESCRIPTION

The present invention is generally directed to ophthalmic lenses (such as IOLs) and methods for correcting vision that employ such lenses. In the embodiments that follow, the salient features of various aspects of the invention are discussed in connection with intraocular lenses (IOLs). The teachings of the invention can also be applied to other ophthalmic lenses, such as contact lenses. The term "intraocular lens" and its abbreviation "IOL" are used herein interchangeably to describe lenses that are implanted into the interior of the eye to either replace the eye's natural lens or to otherwise augment vision regardless of whether or not the natural lens is removed. Intracorneal lenses and phakic intraocular lenses are examples of lenses that may be implanted into the eye without removal of the natural lens. In many embodiments, the lens can include a controlled pattern of surface modulations that selectively impart an optical path difference between an inner and an outer portion of the lens's optic such that the lens would provide sharp images for small and large pupil diameters as well as pseudo-accommodation for viewing objects with intermediate pupil diameters.

Figure 1A:
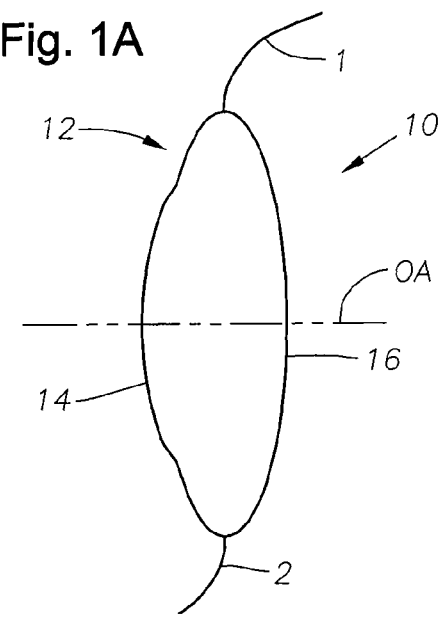
FIG. 1A is a schematic cross-sectional view of an IOL according to an embodiment of the invention.
Figure 1B:
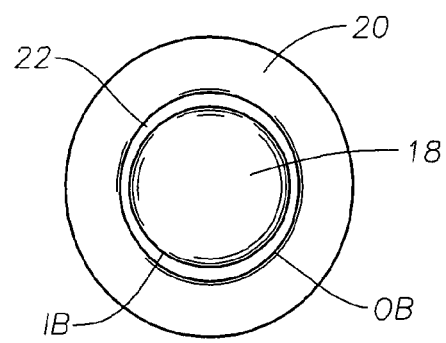
FIG. 1B is schematic top view of the anterior surface of the IOL shown in FIG. 1A, FIG. 2A schematically depicts phase advancement induced in a wavefront incident on a surface of a lens according to one implementation of an embodiment of the invention via a transition region provided on that surface according to the teachings of the invention, FIG. 2B schematically depicts phase delay induced in a wavefront incident on a surface of a lens according to another implementation of an embodiment of the invention via a transition region provided on the surface according to the teachings of the invention, FIG. 3 schematically depicts that the profile of at least a surface of a lens according to an embodiment of the invention can be characterized by superposition of a base profile and an auxiliary profile, FIGS. 4A-4C provide calculated through-focus MTF plots for a hypothetical lens according to an embodiment of the invention for different pupil sizes, FIGS. 5A-5F provide calculated through-focus MTF plots for hypothetical lenses according to some embodiments of the invention, where each lens has a surface characterized by a base profile and an auxiliary profile defining a transition region providing a different Optical Path Difference (OPD) between an inner and an outer region of the auxiliary profile relative to the respective OPD in the other lenses.

FIGS. 1A and 1B schematically depict an intraocular lens (IOL) 10 according to an embodiment of the invention that includes an optic 12 having an anterior surface 14 and a posterior surface 16 that are disposed about an optical axis OA. As shown in FIG. 1B, the anterior surface 14 includes an inner refractive region 18, an outer annular refractive region 20, and an annular transition region 22 that extends between the inner and outer refractive regions. In contrast, the posterior surface 16 is in the form of a smooth convex surface. In some embodiments, the optic 12 can have a diameter D in a range of about 1 mm to about 5 mm, though other diameters can also be utilized.

The exemplary IOL 10 also includes one or more fixation members 1 and 2 (e.g., haptics) that can facilitate its placement in the eye.

In this embodiment, each of the anterior and the posterior surfaces includes a convex base profile, though in other embodiments concave or flat base profiles can be employed. While the profile of the posterior surface is defined solely by a base profile, the profile of the anterior surface is defined by addition of an auxiliary profile to its base profile so as to generate the aforementioned inner, outer and the transition regions, as discussed further below. The base profiles of the two surfaces in combination with the index of refraction of the material forming the optic can provide the optic with a nominal optical power. The nominal optical power can be defined as the monofocal refractive power of a putative optic formed of the same material as the optic 12 with the same base profiles for the anterior and the posterior surface but without the aforementioned auxiliary profile of the anterior surface. The nominal optical power of the optic can also be viewed as the monofocal refractive power of the optic 12 for small apertures with diameters less than the diameter of the central region of the anterior surface.

The auxiliary profile of the anterior surface can adjust this nominal optical power such that the optic's actual optical power, as characterized, e.g. by a focal length corresponding to the axial location of the peak of a through-focus modulation transfer function calculated or measured for the optic at a design wavelength (e.g., 550 nm), would deviate from the lens's nominal optical power, particularly for aperture (pupil) sizes in an intermediate range, as discussed further below. In many embodiments, this shift in the optical power is designed to improve near vision for intermediate pupil sizes. In some cases, the nominal optical power of the optic can be in a range of about −15 D to about +50 D, and preferably in a range of about 6 D to about 34 D. Further, in some cases, the shift caused by the auxiliary profile of the anterior surface to the optic's nominal power can be in a range of about 0.25 D to about 2.5 D.

With continued reference to FIGS. 1A and 1B, the transition region 22 is in the form of an annular region that extends radially from an inner radial boundary (IB) (which in this case corresponds to an outer radial boundary of the inner refractive region 18) to an outer radial boundary (OB) (which in this case corresponds to inner radial boundary of the outer refractive region). While in some cases, one or both boundaries can include a discontinuity in the anterior surface profile (e.g., a step), in many embodiments the anterior surface profile is continuous at the boundaries, though a radial derivative of the profile (that is, the rate of change of the surface sag as a function of radial distance from the optical axis) can exhibit a discontinuity at each boundary. In some cases, the annular width of the transition region can be in a range of about 0.75 mm to about 2.5 nm. In some cases, the ratio of an annular width of the transition region relative to the radial diameter of the anterior surface can be in a range of about 0 to about 0.2.

In many embodiments, the transition region 22 of the anterior surface 14 can be shaped such that a phase of radiation incident thereon would vary monotonically from its inner boundary (IB) to its outer boundary (OB). That is, a non-zero phase difference between the outer region and the inner region would be achieved via a progressive increase or a progressive decrease of the phase as a function of increasing radial distance from the optical axis across the transition region. In some embodiments, the transition region can include plateau portions, interspersed between portions of progressive increase or decrease of the phase, in which the phase can remain substantially constant.

In many embodiments, the transition region is configured such that the phase shift between two parallel rays, one of which is incident on the outer boundary of the transition region and the other is incident on the inner boundary of the transition region, can be a non-integer rational fraction of a design wavelength (e.g., a design wavelength of 550 nm). By way of example, such a phase shift can be defined in accordance with the following relation:

$$\text{Phase shift} = \frac{2\pi}{\lambda} OPD, \quad \text{Eq. (1A)}$$

$$OPD = (A + B)\lambda \quad \text{Eq. (1B)}$$

wherein,
A designates an integer,
B designates a non-integer rational fraction, and
λ designates a design wavelength (e.g., 550 nm).
By way of example, the total phase shift across the transition region can be $$\frac{\lambda}{2}, \frac{\lambda}{3},$$

etc, where λ represents a design wavelength, e.g., 550 nm. In many embodiments, the phase shift can be a periodic function of the wavelength of incident radiation, with a periodicity corresponding to one wavelength.

In many embodiments, the transition region can cause a distortion in the wavefront emerging from the optic in response to incident radiation (that is, the wavefront emerging from the posterior surface of the optic) that can result in shifting the effective focusing power of the lens relative to its nominal power. Further, the distortion of the wavefront can enhance the optic's depth of focus for aperture diameters that encompass the transition region, especially for intermediate diameter apertures, as discussed further below. For example, the transition region can cause a phase shift between the wavefront emerging from the outer portion of the optic and that emerging from its inner portion. Such a phase shift can cause the radiation emerging from optic's outer portion to interfere with the radiation emerging from the optic's inner portion at the location at which the radiation emerging from the optic's inner portion would focus, thus resulting in an enhanced depth-of-focus, e.g., as characterized by an asymmetric MTF (modulation transfer function) profile referenced to the peak MTF. The term "depth-of-focus" and "depth-of-field" can be used interchangeably and are known and readily understood by those skilled in the art as referring to the distances in the object and image spaces over which an acceptable image can be resolved. To the extent that any further explanation may be needed, the depth-of-focus can refer to an amount of defocus relative to a peak of a through-focus modulation transfer function (MTF) of the lens measured with a 3 mm aperture and green light, e.g., light having a wavelength of about 550 nm, at which the MTF exhibits a contrast level of at least about 15% at a spatial frequency of about 50 lp/mm. Other definitions can also be applied and it should be clear that depth of field can be influenced by many factors including, for example, aperture size, chromatic content of the light forming the image, and base power of the lens itself.

Figure 2A:
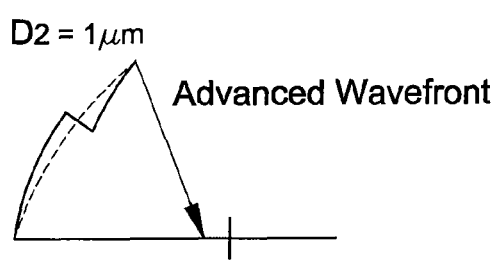
Figure 2B:
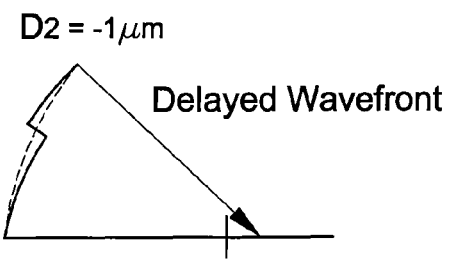

By way of further illustration, FIG. 2A schematically shows a fragment of a wavefront generated by an anterior surface of an IOL according to an embodiment of the invention having a transition region between an inner portion and an outer portion of the surface, and a fragment of a wavefront incident on that surface, and a reference spherical wavefront (depicted by dashed lines) that minimizes the RMS (root-mean-square) error of the actual wavefront. The transition region gives rise to a phase advancement of the wavefront (relative to that corresponding to a putative similar surface without the transition region) that leads to the convergence of the wavefront at a focal plane in front of the retinal plane (in front of the nominal focal plane of the IOL in absence of the transition region). FIG. 2B schematically shows another case in which the transition region gives rise to a phase delay of an incident wavefront that leads to the convergence of the wavefront at a focal plane beyond the retinal plane (beyond the nominal focal plane of the IOL in absence of the transition region).

By way of illustration, in this implementation, the base profile of the anterior and/or the posterior surfaces can be defined by the following relation:

$$z_{base} = \frac{cr^2}{1 + \sqrt{1 - (1+k)c^2 r^2}} + f(r^2, r^4, r^6, \dots) \quad \text{Eq. (2)}$$

wherein,
c denotes the curvature of the profile,
k denotes the conic constant, and
wherein,
$f(r^2, r^4, r^6, \dots)$ denotes a function containing higher order contributions to the base profile. By way of example, the function $f$ can be defined by the following relation:

$$f(r^2, r^4, r^6, \dots) = a_2 r^2 + a_4 r^4 + a_6 r^6 + \dots \quad \text{Eq. (3)}$$

wherein, $a_2$ is a second order deformation constant, $a_4$ is a fourth order deformation constant, and $a_6$ is a sixth order deformation constant. Additional higher order terms can also be included.

By way of example, in some embodiments, the parameter c can be in a range of about 0.0152 mm$^{-1}$ to about 0.0659 mm$^{-1}$, the parameter k can be in range of about −1162 to about −19, $a_2$ can be in a range of about −0.00032 mm$^{-1}$ to about 0.0 mm$^{-1}$, $a_4$ can be in a range of about 0.0 mm$^{-3}$ to about −0.000053 (minus 5.3×10$^{-5}$) mm$^{-3}$, and $a_6$ can be in a range of about 0.0 mm$^{-5}$ to about 0.000153 (1.53×10$^{-4}$) mm$^{-5}$.

The use of certain degree of asphericity in the anterior and/or posterior base profile as characterized, e.g., by the conic constant k, can ameliorate spherical aberration effects for large aperture sizes. For large aperture sizes, such asphericity can somewhat degree counteract the optical effects of the transition region, thus leading to a shaper MTF. In some other embodiments, the base profile of one or both surfaces can be toric (that is, it can exhibit different radii of curvatures along two orthogonal directions along the surface) to ameliorate astigmatic aberrations.

As noted above, in this exemplary embodiment, the profile of the anterior surface 14 can be defined by superposition of a base profile, such as the profile defined by the above Equation (1), and an auxiliary profile. In this implementation, the auxiliary profile ($Z_{aux}$) can be defined by the following relation:

$$Z_{aux} = \begin{cases} 0, & 0 \leq r < r_1 \\ \frac{\Delta}{(r_2 - r_1)}(r - r_1), & r_1 \leq r < r_2 \\ \Delta, & r_2 < r \end{cases} \quad \text{Eq. (4)}$$

wherein, $r_1$ denotes an inner radial boundary of the transition region, $r_2$ denotes an outer radial boundary of the transition region, and wherein, $\Delta$ is defined by the following relation:

$$\Delta = \frac{\alpha \lambda}{(n_2 - n_1)}, \quad \text{Eq. (5)}$$

wherein, $n_1$ denotes an index of refraction of material forming the optic, $n_2$ denotes an index of refraction of a medium surrounding the optic, $\lambda$ denotes a design wavelength, and $\alpha$ denotes a non-integer fraction, e.g., ½.

In other words, in this embodiment, the profile of the anterior surface ($Z_{sag}$) is defined by a superposition of the base profile ($Z_{base}$) and the auxiliary profile ($Z_{aux}$) as defined below, and shown schematically in FIG. 3:

$$Z_{sag} = Z_{base} + Z_{aux} \quad \text{Eq. (6)}$$

In this embodiment, the auxiliary profile defined by the above relations (4) and (5) is characterized by a substantially linear phase shift across the transition region. More specifically, the auxiliary profile provides a phase shift that increases linearly from the inner boundary of the transition region to its outer boundary with the optical path difference between the inner and the outer boundaries corresponding to a non-integer fraction of the design wavelength.

In many embodiments, a lens according to the teachings of the invention, such the above lens 10, can provide good far vision performance by effectively functioning as a monofocal lens without the optical effects caused by the phase shift for small pupil diameters that fall within the diameter of the lens's central region (e.g., for a pupil diameter of 2 mm). For medium pupil diameters (e.g., for pupil diameters in a range of about 2 mm to about 4 mm (e.g., a pupil diameter of about 3 mm)), the optical effects caused by the phase shift (e.g., changes in the wavefront exiting the lens) can lead to enhanced functional near and intermediate vision. For large pupil diameters (e.g., for pupil diameters in a range of about 4 mm to about 5 mm), the lens can again provide good far vision performance as the phase shift would only account for a small fraction of the anterior surface portion that is exposed to incident light.

Figure 4A:
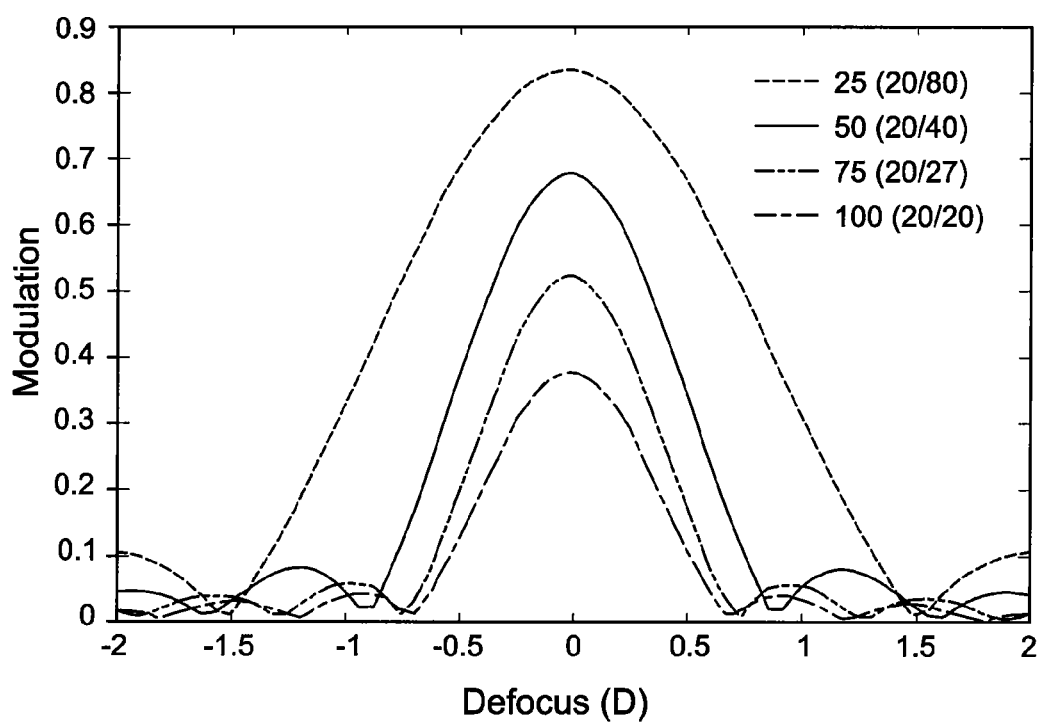
Figure 4B:
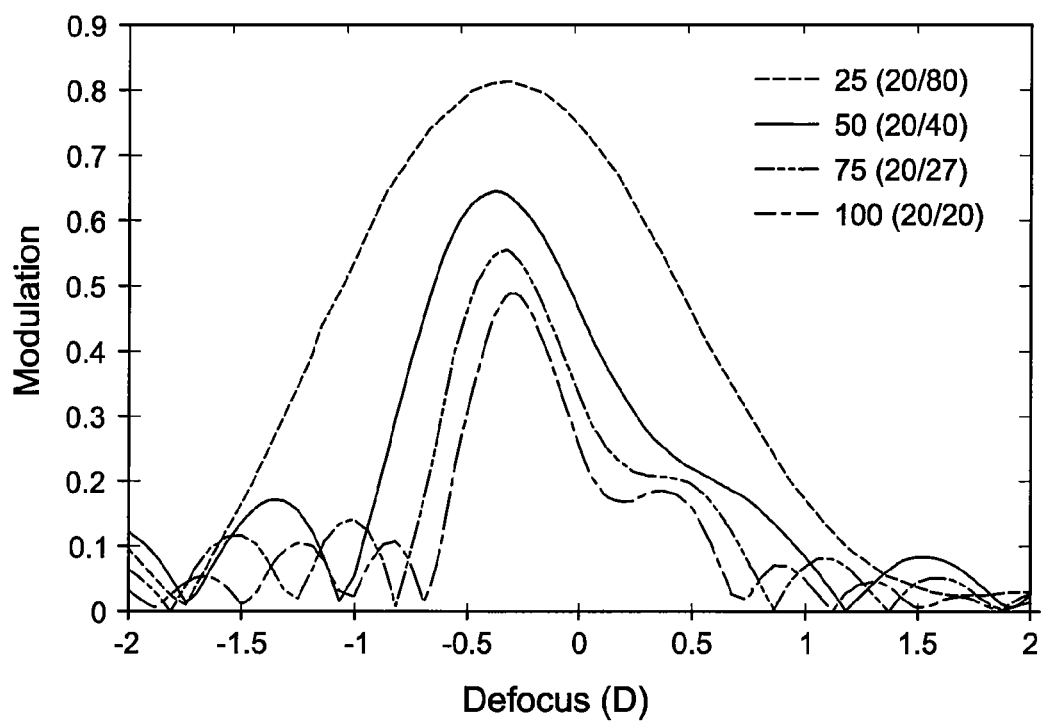
Figure 4C:
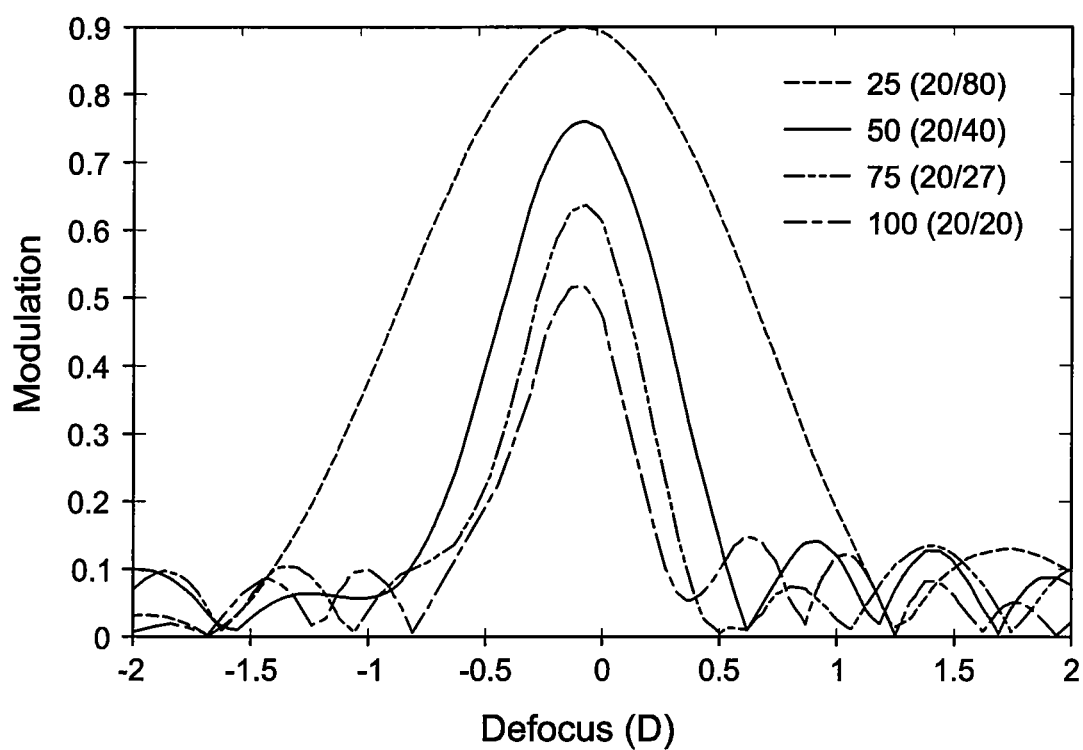

By way of illustration, FIG. 4A-4C show optical performance of a hypothetical lens according to an embodiment of the invention for different pupil sizes. The lens was assumed to have an anterior surface defined by the above relation (6), and a posterior surface characterized by a smooth convex base profile (e.g., one defined by that above relation (2)). Further, the lens was assumed to have a diameter of 6 mm with the transition region extending between an inner boundary having a diameter of about 2.2 mm to an outer boundary having a diameter of about 2.6 mm. The base curvatures of the anterior and the posterior surface were selected such that the optic would provide a nominal optical power of 21 D. Further, the medium surrounding the lens was assumed to have an index of refraction of about 1.336. Tables 1A-1C below list the various parameters of the lens's optic as well as those of its anterior and posterior surfaces:

TABLE 1A

| Optic | | |
|---|---|---|
| Central Thickness (mm) | Diameter (mm) | Index of Refraction |
| 0.64 | 6 | 1.5418 |

TABLE 1B

Anterior Surface

| Base Profile | | | | | Auxiliary Profile | | |
|---|---|---|---|---|---|---|---|
| Base Radius (mm) | Conic Constant (k) | $a_2$ | $a_4$ | $a_6$ | r1 | r2 | Δ |
| 18.93 | −43.56 | 0 | 2.97E−4 | −2.3E−5 | 1.1 | 1.25 | −1.18 |

TABLE 1C

| Posterior Surface | | | | |
|---|---|---|---|---|
| Base Radius (mm) | Conic Constant (k) | $a_2$ | $a_4$ | $a_6$ |
| −20.23 | 0 | 0 | 0 | 0 |

More specifically, in each of the FIGS. 4A-4C, through-focus modulation transfer (MTF) plots corresponding to the following modulation frequencies are provided: 25 lp/mm, 50 lp/mm, 75 lp/mm, and 100 lp/mm. The MTF shown in FIG. 4A for a pupil diameter of about 2 mm indicates that the lens provides good optical performance, e.g., for outdoor activities, with a depth-of focus of about 0.7 D, which is symmetric about the focal plane. For a pupil diameter of 3 mm, each of the MTFs shown in FIG. 4B is asymmetric relative to the lens's focal plane (i.e., relative to zero defocus) with a shift in its peak in the negative defocus direction. Such a shift can provide a degree of pseudoaccommodation to facilitate near vision (e.g., for reading). Further, these MTFs have greater widths than those shown by the MTFs calculated for a 2-mm pupil diameter, which translates to better performance for intermediate vision. For a larger pupil diameter of 4 mm (FIG. 4C), the asymmetry and the widths of the MTFs diminish relative to those calculated for a 3-mm diameter. This in turn indicates good far vision performance under low light conditions, e.g., for night driving.

The optical effect of the phase shift can be modulated by varying various parameters associated with that region, such as, its radial extent and the rate at which it imparts phase shift to incident light. By way of example, the transition region defined by the above relation (3) exhibits a slope defined by $$\frac{\Delta}{(r_2 - r_1)},$$

which can be varied so as to adjust the performance of an optic having such a transition region on a surface thereof, particularly for intermediate pupil sizes.

Figure 3:
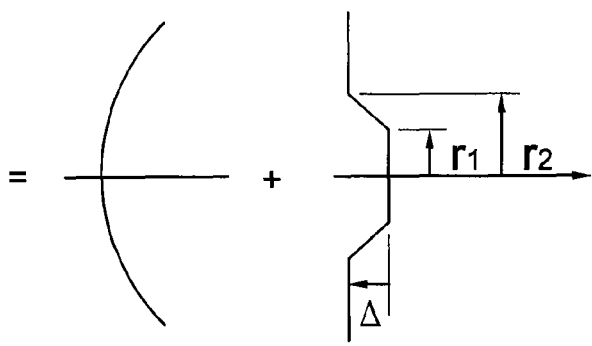

By way of illustration, FIGS. 5A-5F show calculated through-focus modulation transfer function (MTF) at a pupil size of 3 mm and for a modulation frequency of 50 lp/mm for hypothetical lenses having an anterior surface exhibiting the surface profile shown in FIG. 3 as a superposition of a base profile defined by the relation (2) and an auxiliary profile defined by the relations (4) and (5). The optic was assumed to be formed of a material having an index of refraction of 1.554. Further, the base curvature of the anterior surface and that of the posterior surface were selected such that the optic would have a nominal optical power of about 21 D.

Figure 5A:
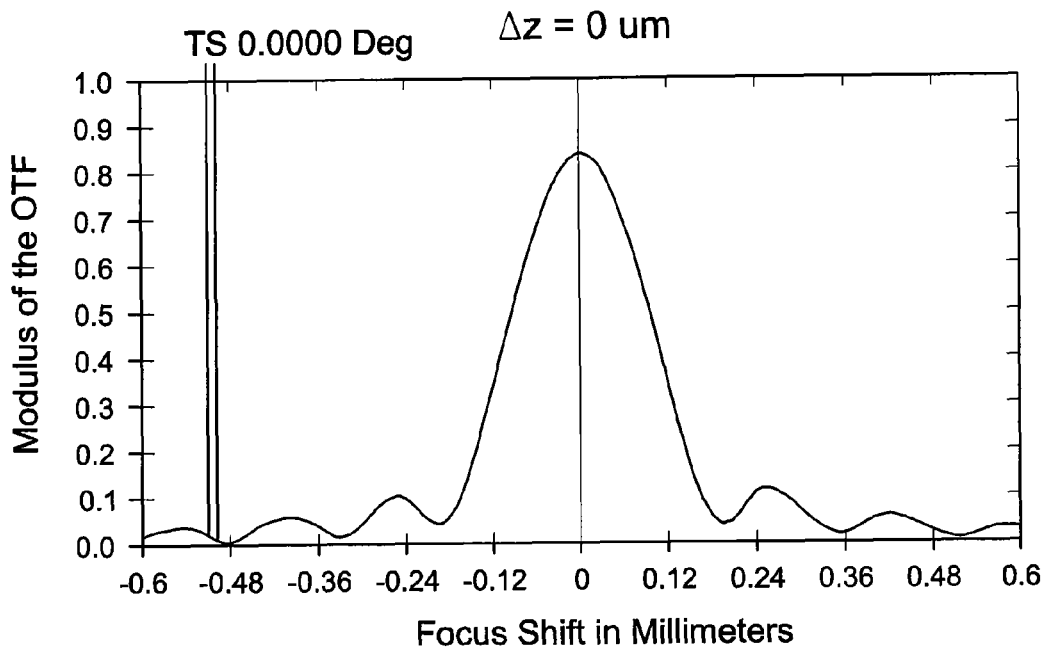
Figure 5B:
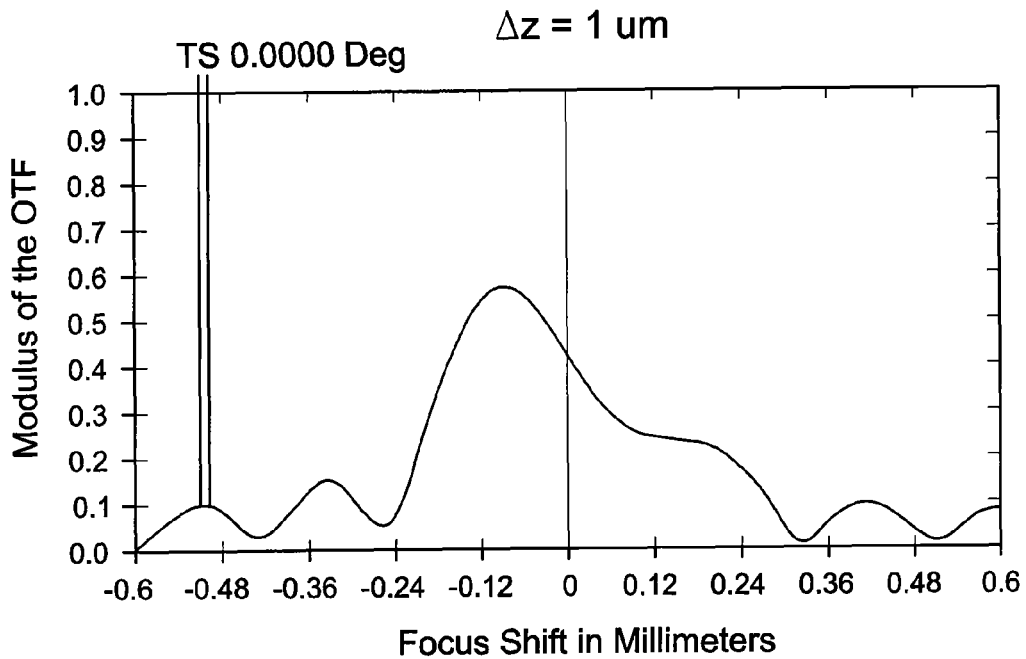
Figure 5C:
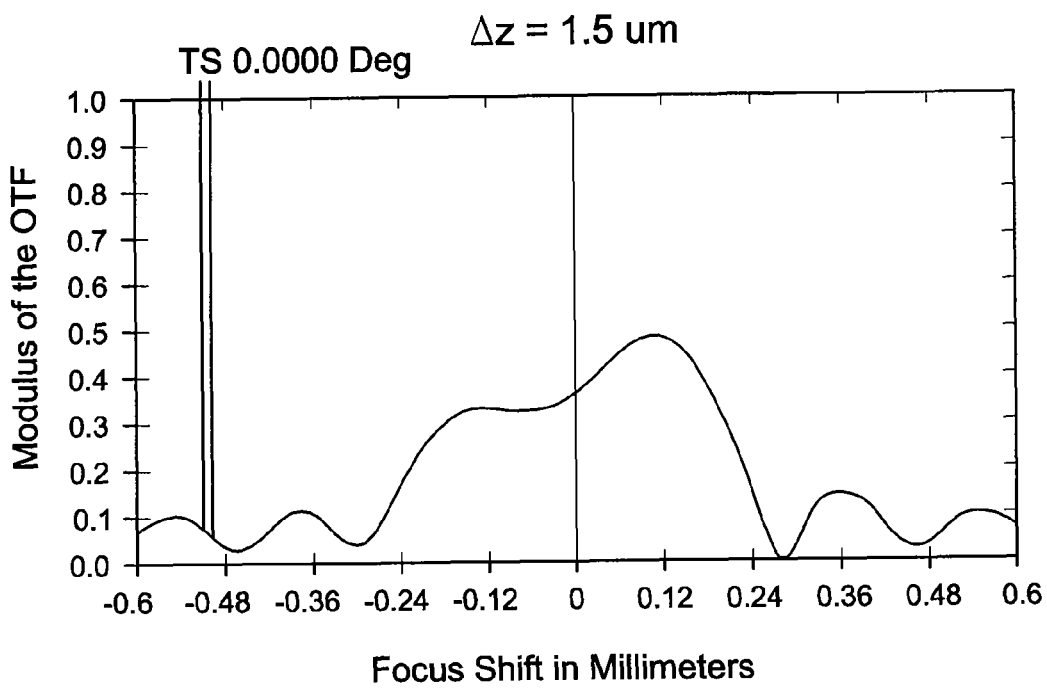

By way of providing a reference from which the optical effects of the transition region can be more readily understood, FIG. 5A shows an MTF for an optic having a vanishing $\Delta z$, that is, an optic that lacks a phase shift according to the teachings of the invention. Such a conventional optic having smooth anterior and posterior surfaces exhibits an MTF curve that is symmetrically disposed about the optic's focal plane and exhibits a depth of focus of about 0.4 D. In contrast, FIG. 5B shows an MTF for an optic according to an embodiment of the invention in which the anterior surface includes a transition region characterized by a radial extent of about 0.01 mm and $\Delta z=1$ micron. The MTF plot shown in FIG. 5B exhibits a greater depth of focus of about 1 D, indicating that the optic provides an enhanced depth of field. Further, it is asymmetric relative to the optic's focal plane. In fact, the peak of this MTF plot is closer to the optic than its focal plane. This provides an effective optical power increase to facilitate near reading.

Figure 5D:
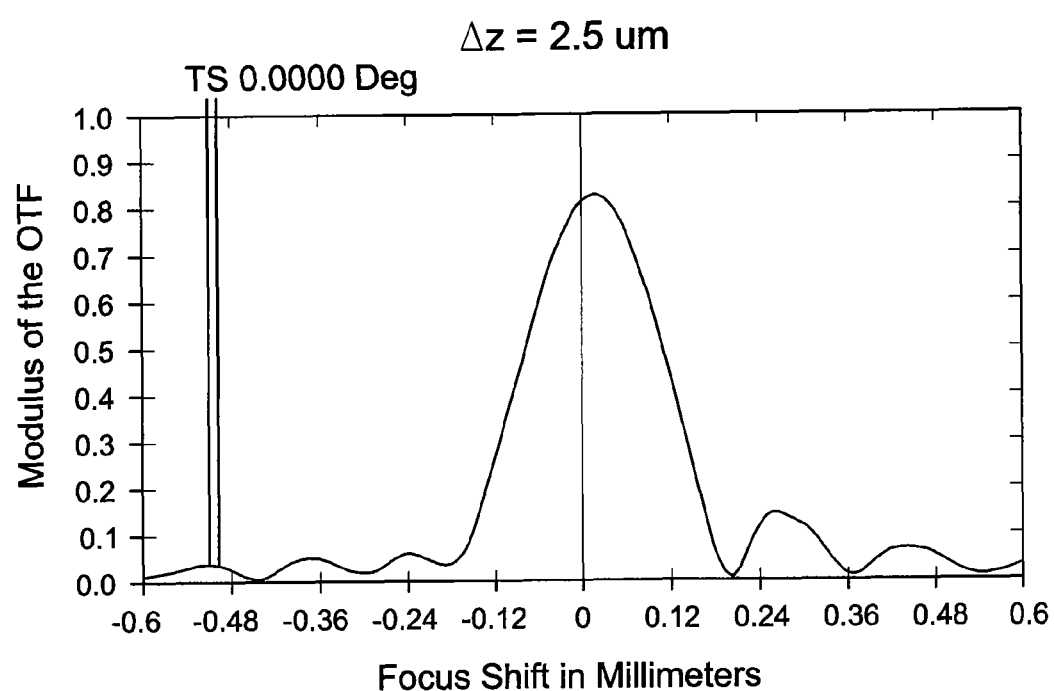
Figure 5E:
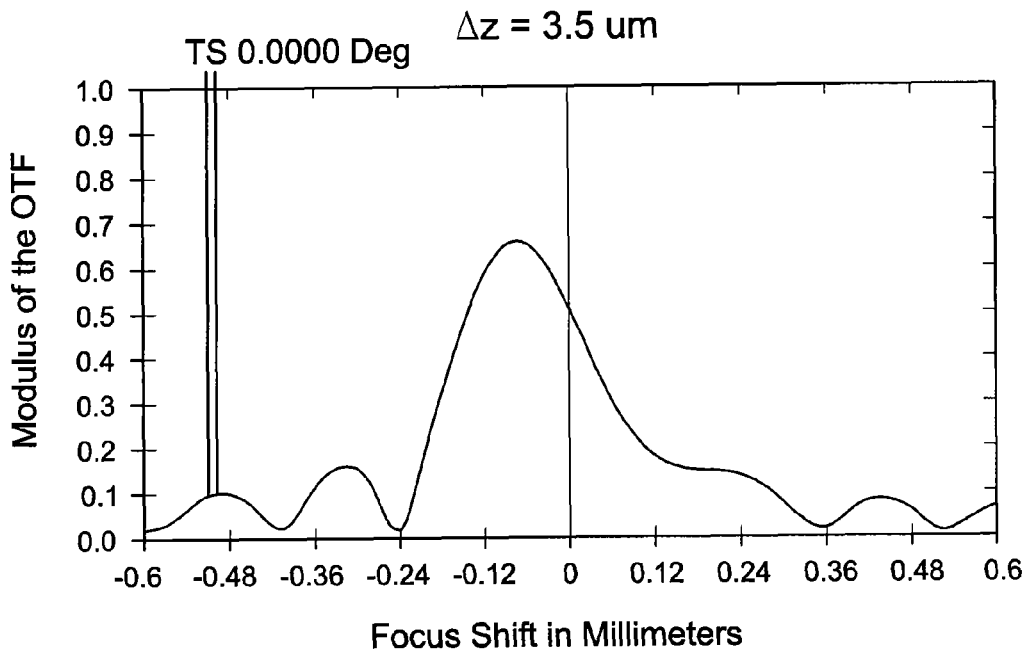
Figure 5F:
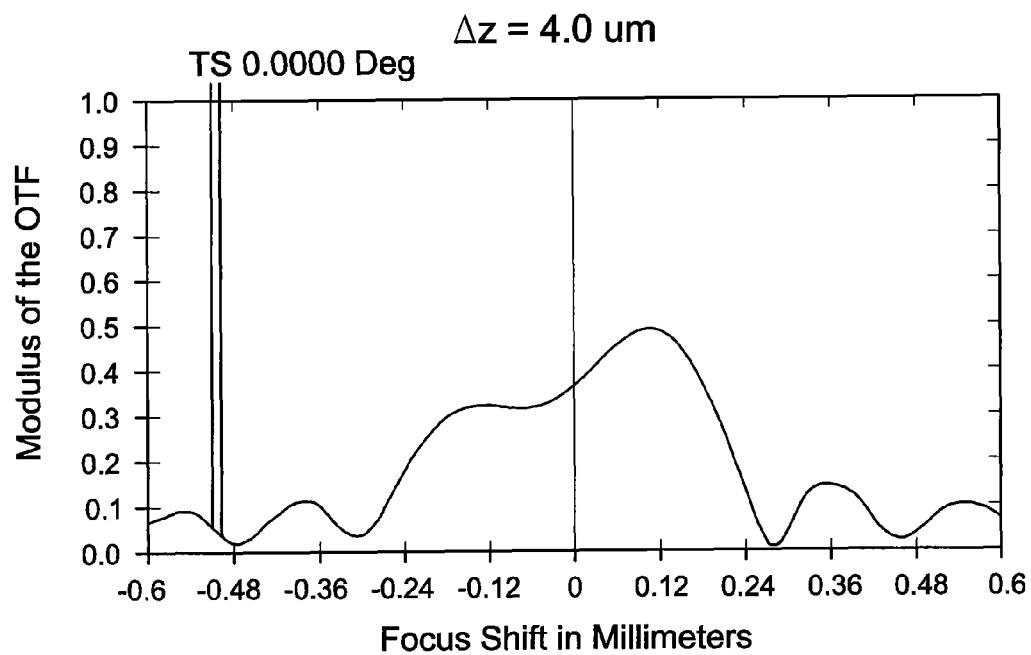

As the transition region becomes steeper (its radial extent remains fixed at 0.01 mm) so as to provide a $\Delta Z=1.5$ microns (FIG. 5C), the MTF broadens further (that is, the optic provides a greater depth-of-field) and its peak shifts farther away from the optic than the optic's focal plane. As shown in FIG. 5D, the MTF for an optic having a transition region characterized by a $\Delta Z=2.5$ microns is identical to the one shown in FIG. 5A for an optic having a $\Delta Z=0$.

In fact, the MTF pattern is repeated for every design wavelength. By way of example, in an embodiment in which the design wavelength is 550 nm and the optic is formed of Acrysof material (cross-linked copolymer of 2-phenylethyl acrylate and 2-phenylethyl methacrylate) $\Delta Z=2.5$ microns. For example, the MTF curve shown in FIG. 5E corresponding to a $\Delta Z=3.5$ microns is identical to that shown in FIG. 5B for a $\Delta Z=1.5$, and the MTF curve shown in FIG. 5F corresponding to a $\Delta Z=4$ microns is identical to the MTF curve shown in FIG. 5C corresponding to a $\Delta Z=1.5$ microns. The optical path difference (OPD) corresponding to $\Delta Z$ for $Z_{aux}$ defined by the above relation (3) can be defined by the following relation:

$$\text{Optical Path Difference (OPD)} = (n_2 - n_1)\Delta Z \qquad \text{Eq. (7)}$$

wherein $n_1$ represent the index of refraction of the material from which the optic is formed, and $n_2$ represents the index of refraction of the material surrounding the optic. Thus, for $n_2=1.552$, and $n_1=1.336$, and a $\Delta Z$ of 2.5 microns, an OPD corresponding to $1\lambda$ is achieved for a design wavelength of about 550 nm. In other words, the exemplary MTF plots shown in FIGS. 5A-5F are repeated for a $\Delta Z$ variation corresponding to $1\lambda$ OPD.

A transition region according to the teachings of the invention can be implemented in a variety of ways, and is not restricted to the above exemplary region that is defined by the relation (4). Further, while in some cases the transition region comprises a smoothly varying surface portion, in other cases it can be formed by a plurality of surface segments separated from one another by one or more steps.

Figure 6:
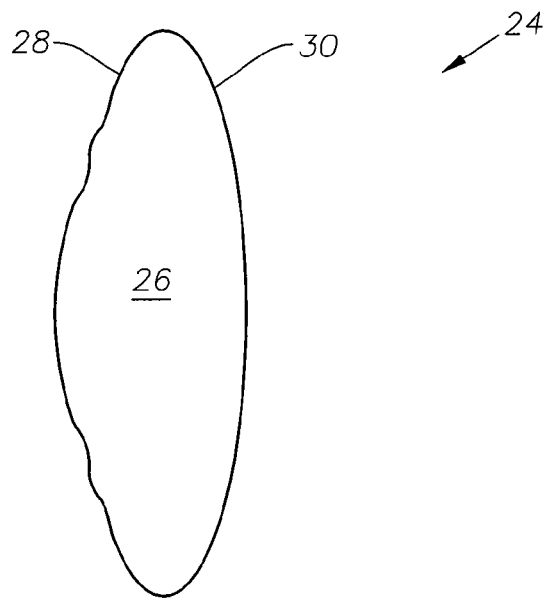
FIG. 6 is a schematic cross-sectional view of an IOL according to another embodiment of the invention, and FIG. 7 schematically depicts that the profile of the anterior surface can be characterized as a superposition of a base profile and an auxiliary profile that includes a two-step transition region.

FIG. 6 schematically depicts an IOL 24 according to another embodiment of the invention that includes an optic 26 having an anterior surface 28 and a posterior surface 30. Similar to the previous embodiment, the profile of the anterior surface can be characterized as the superposition of a base profile and an auxiliary profile, albeit one that is different from the auxiliary profile described above in connection with the previous embodiment.

Figure 7:
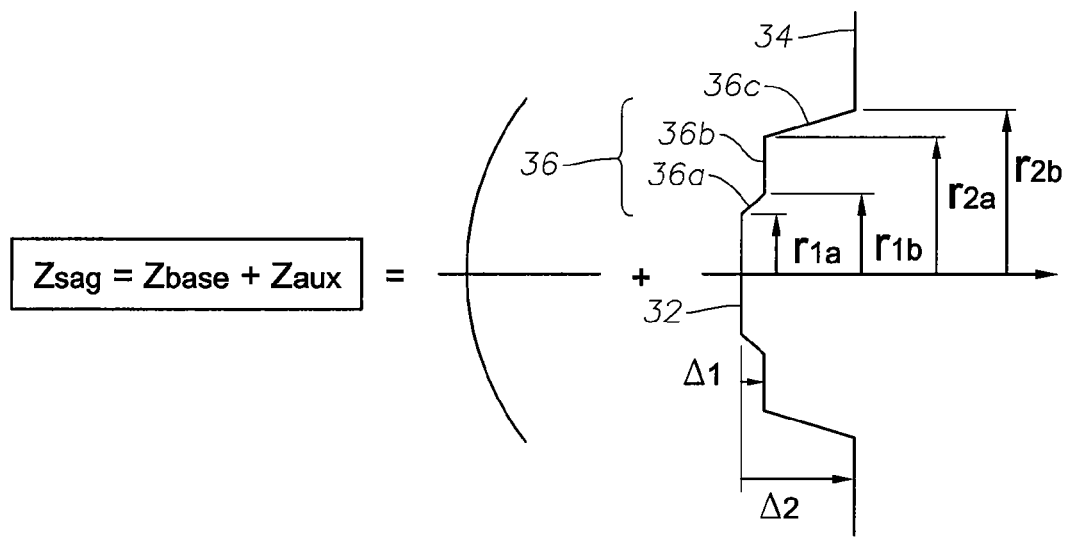

As shown schematically in FIG. 7, the profile ($Z_{sag}$) of the anterior surface 28 of the above IOL 24 is formed by superposition of a base profile ($Z_{base}$) and an auxiliary profile ($Z_{aux}$). More specifically, in this implementation, the profile of the anterior surface 28 can be defined by the above relation (6), which is reproduced below:

$$Z_{sag} = Z_{base} + Z_{aux}$$

wherein the base profile ($Z_{base}$) can be defined in accordance with the above relation (2). The auxiliary profile ($Z_{aux}$) is, however, defined by the following relation:

$$z_{aux} = \begin{cases} 0, & 0 \le r < r_{1a} \\ \frac{\Delta_1}{(r_{1b} - r_{1a})}(r - r_{1a}), & r_{1a} \le r < r_{1b} \\ \Delta_1, & r_{1b} \le r < r_{2a} \\ \Delta_1 + \frac{(\Delta_2 - \Delta_1)}{(r_{2b} - r_{2a})}(r - r_{2a}), & r_{2a} \le r < r_{2b} \\ \Delta_2 & r_{2b} < r \end{cases} \qquad \text{Eq. (8)}$$

wherein r denotes the radial distance from an optical axis of the lens, and parameters $r_{1a}$, $r_{1b}$, $r_{2a}$ and $r_{2b}$ are depicted in FIG. 7, and are defined as follows:

$r_{1a}$ denotes the inner radius of a first substantially linear portion of the transition region of the auxiliary profile, $r_{1b}$ denotes the outer radius of the first linear portion, $r_{2a}$ denotes the inner radius of a second substantially linear portion of the transition region of the auxiliary profile, and $r_{2b}$ denotes the outer radius of the second linear portion, and wherein each of $\Delta_1$ and $\Delta_2$ can be defined in accordance with the above relation (8).

TABLE 2A

| Optic | | |
|---|---|---|
| Central Thickness (mm) | Diameter (mm) | Index of Refraction |
| 0.64 | 6 | 1.5418 |

TABLE 2B

| Anterior Surface | | | | | | | | | |
|---|---|---|---|---|---|---|---|---|---|
| Base Profile | | | | | Auxiliary Profile | | | | |
| Base Radius (mm) | Conic Constant | $a_2$ | $a_4$ | $a_6$ | $r_{1a}$ (mm) | $r_{1b}$ (mm) | $r_{2a}$ (mm) | $r_{2b}$ (mm) | $\Delta_1$ (micron) | $\Delta_2$ (micron) |
| 18.93 | −43.564 | 0 | 2.97E−4 | −2.3E−5 | 1.0 | 1.01 | 1.25 | 1.26 | 0.67 | 2.67 |

With continued reference to FIG. 7, in this embodiment, the auxiliary profile $Z_{aux}$ includes flat central and outer regions 32 and 34 and a two-step transition 36 that connects the central and the outer regions. More specifically, the transition region 36 includes a linearly varying portion 36a, which extends from an outer radial boundary of the central region 32 to a plateau region 36b (it extends from a radial location $r_{1a}$ to another radial location $r_{1b}$). The plateau region 36b in turn extends from the radial location $r_{1b}$ to a radial location $r_{2a}$ at which it connects to another linearly varying portion 36c, which extends radially outwardly to the outer region 34 at a radial location $r_{2b}$. The linearly varying portions 36a and 36c of the transition region can have similar or different slopes. In many implementations, the total phase shift provided across the two transition regions is a non-integer fraction of a design wavelength (e.g., 550 nm).

The profile of the posterior surface 30 can be defined by the above relation (2) for $Z_{base}$ with appropriate choices of the various parameters, including the radius of curvature c. The radius curvature of the base profile of the anterior surface together with the curvature of the posterior surface, as well as the index of refraction of the material forming the lens, provides the lens with a nominal refractive optical power, e.g., an optical power in a range of about −15 D to about +50 D, or in a range of about 6 D to about 34 D, or in a rang of about 16 D to about 25 D.

Figure 8:
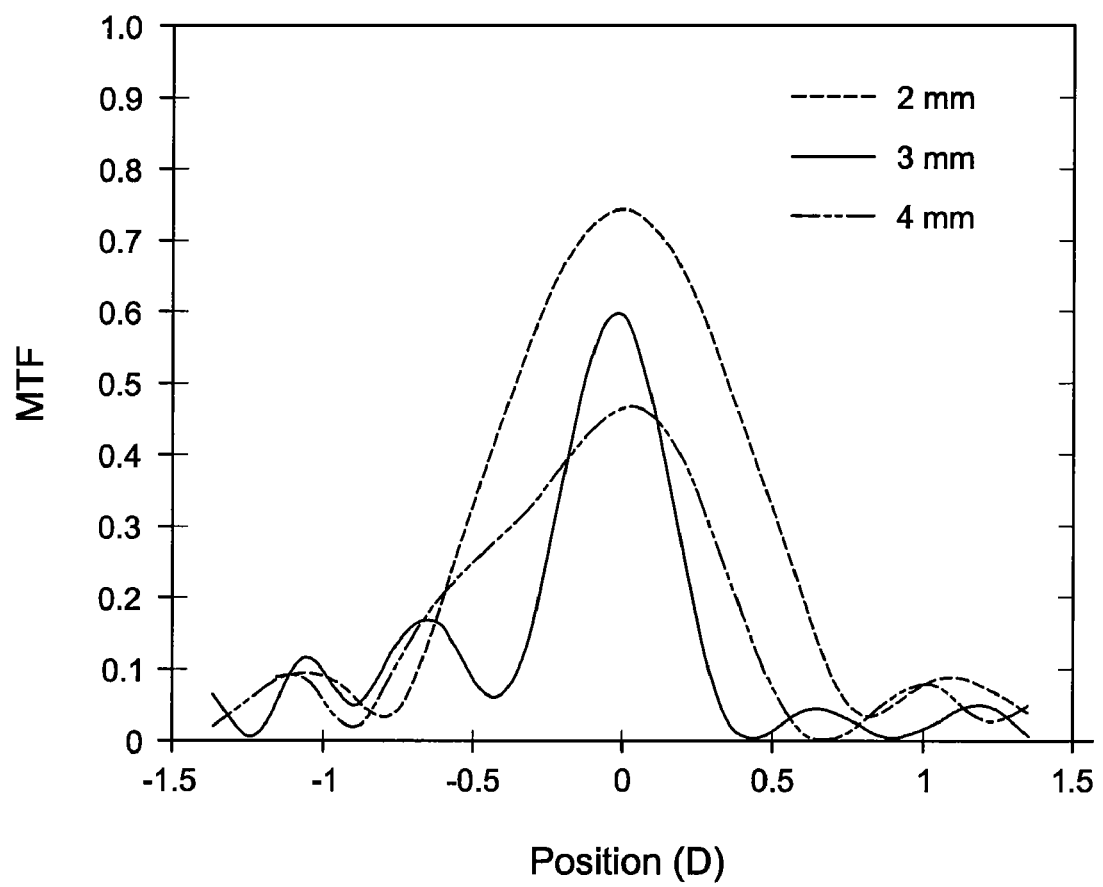
FIG. 8 presents calculated through-focus monochromatic MTF plots for a hypothetical lens according to an embodiment of the invention having a two-step transition region.

The exemplary IOL 24 can provide a number of advantages. For example, it can provide sharp far vision for small pupil sizes with the optical effects of the two-step transition region contributing to the enhancement of functional near and intermediate vision. Further, in many implementations, the IOL provides good far vision performance for large pupil sizes. By way of illustration, FIG. 8 shows through-focus MTF plots at different pupil sizes calculated for a hypothetical optic according to an embodiment of the invention having an anterior surface whose profile is defined by the above relation (2) with the auxiliary profile of the anterior surface defined by the above relation (8) and a smooth convex posterior surface. The MTF plots are computed for monochromatic incident radiation having a wavelength of 550 nm. Tables 2A-2C below provide the parameters of the anterior and the posterior surfaces of the optic:

TABLE 2C

| Posterior Surface | | | | |
|---|---|---|---|---|
| Base Radius (mm) | Conic Constant (k) | $a_2$ | $a_4$ | $a_6$ |
| −20.23 | 0 | 0 | 0 | 0 |

The MTF plots show that for a pupil diameter of about 2 mm, which is equal to the diameter of the central portion of the anterior surface, the optic provides a monofocal refractive power and exhibits a relatively small depth of focus (defined as full width at half maximum) of about 0.5 D. In other words, it provides good far vision performance. As the pupil size increases to about 3 mm, the optical effects of the transition region become evident in the through-focus MTF. In particular, the 3-mm MTF is significantly broader than the 2-mm MTF, indicating an enhancement in the depth-of-field.

With continued reference to FIG. 8, as the pupil diameter increases even further to about 4 mm the incident light rays encounter not only the central and the transition regions but also part of the outer region of the anterior surface.

A variety of techniques and materials can be employed to fabricate the IOLs of the invention. For example, the optic of an IOL of the invention can be formed of a variety of biocompatible polymeric materials. Some suitable biocompatible materials include, without limitation, soft acrylic polymers, hydrogel, polymethylmethacrylate, polysulfone, polystyrene, cellulose, acetate butyrate, or other biocompatible materials. By way of example, in one embodiment, the optic is formed of a soft acrylic polymer (cross-linked copolymer of 2-phenylethyl acrylate and 2-phenylethyl methacrylate) commonly known as Acrysof. The fixation members (haptics) of the IOLs can also be formed of suitable biocompatible materials, such as those discussed above. While in some cases, the optic and the fixation members of an IOL can be fabricated as an integral unit, in other cases they can be formed separately and joined together utilizing techniques known in the art.

A variety of fabrication techniques known in the art, such as a casting, can be utilized for fabricating the IOLs. In some cases, the fabrication techniques disclosed in pending patent application entitled "Lens Surface With Combined Diffractive, Toric and Aspheric Components," filed on Dec. 21, 2007 and having a Ser. No. 11/963,098 can be employed to impart desired profiles to the anterior and posterior surfaces of the IOL.

Those having ordinary skill in the art will appreciate that various changes can be made to the above embodiments without departing from the scope of the invention.

The invention claimed is:

1. A monofocal intraocular lens, comprising:
an optic having an anterior surface and a posterior surface disposed about an optical axis, at least one of said surfaces being toric and at least one of said surfaces comprising:
  at least one inner refractive region having a nominal optical power,
  at least one outer refractive region having the nominal optical power, and
  a refractive transition region disposed between said inner and outer regions, said transition region extending from an inner radial boundary to an outer radial boundary thereof,
wherein said transition region is adapted such that a phase of radiation incident thereon varies monotonically from said inner to said outer boundary so as to generate a phase shift between said outer and inner boundaries characterized by a selected non-integer fraction of a design wavelength in the visible spectrum such that a first portion of an incoming wavefront in the inner refractive region and a second portion of the incoming wavefront in the outer refractive region converge to produce an effective optical power different from the nominal optical power thereby creating a depth of focus.

2. The intraocular lens of claim 1, wherein the transition region is adapted to provide a monotonic change in optical path difference relative to the outer boundary of the inner region as a function of increasing radial distance from the optical axis.

3. The intraocular lens of claim 2, wherein the monotonic change is characterized by a linear change in surface height $Z_{tps}$ relative to a refractive surface defining the nominal optical power as follows:

$$Z_{tps} = \begin{cases} 0, & 0 \leq r < r_1 \\ \frac{\Delta}{(r_2 - r_1)}(r - r_1), & r_1 \leq r < r_2 \\ \Delta, & r_2 < r \end{cases}$$

wherein,
$r_1$ denotes an inner radial boundary of the transition region,
$r_2$ denotes an outer radial boundary of the transition region, and
wherein,
$\Delta$ is defined by the following relation:

$$\Delta = \frac{\alpha \lambda}{(n_2 - n_1)},$$

wherein,
$n_1$ denotes an index of refraction of material forming the optic,
$n_2$ denotes an index of refraction of a medium surrounding the optic when positioned for use in or on an eye,
$\lambda$ denotes the design wavelength, and
$\alpha$ denotes the selected non-integer fraction.

4. The intraocular lens of claim 2, wherein the monotonic change is characterized by a succession of linear changes separated by one or more plateaus and wherein a change in surface height $z_{aux}$ relative to a refractive surface defining the nominal optical power is as follows:

$$z_{aux} = \begin{cases} 0, & 0 \leq r < r_{1a} \\ \frac{\Delta_1}{(r_{1b} - r_{1a})}(r - r_{1a}), & r_{1a} \leq r < r_{1b} \\ \Delta_1, & r_{1b} \leq r < r_{2a} \\ \Delta_1 + \frac{(\Delta_2 - \Delta_1)}{(r_{2b} - r_{2a})}(r - r_{2a}), & r_{2a} \leq r < r_{2b} \\ \Delta_2 & r_{2b} < r \end{cases}$$

wherein
r denotes the radial distance from an optical axis of the lens,
$r_{1a}$ denotes a radius of a first substantially linear portion of the transition region,
$r_{1b}$ denotes the outer radius of the first linear portion,
$r_{2a}$ denotes an inner radius of a second substantially linear portion of the transition region, and
$r_{2b}$ denotes an outer radius of the second substantially linear portion, and
wherein
each of $\Delta_1$ and $\Delta_2$ can is defined in accordance with the following relation:

$$\Delta_1 = \frac{\alpha_1 \lambda}{(n_2 - n_1)},$$

and $$\Delta_2 = \frac{\alpha_2 \lambda}{(n_2 - n_1)}$$

wherein,
n1 denotes an index of refraction of material forming the optic,
n2 denotes an index of refraction of a medium surrounding the optic,
$\lambda$ denotes the design wavelength,
$\alpha_1$ denotes a first non-integer fraction, and
$\alpha_2$ denotes a second non-integer fraction, the sum of the first and second non-integer fractions being the selected non-integer fraction.

5. The intraocular lens of claim 1, wherein the selected non-integer fraction is less than one.

6. The intraocular lens of claim 1, wherein the selected non-integer fraction is greater than one.

7. The intraocular lens of claim 1, wherein said transition region comprises an annular region.

8. The intraocular lens of claim 7, wherein the annular region has a radial width less than about 1 mm.

9. The intraocular lens of claim 1, wherein at least one of the at least one surfaces has a radial diameter in a range of about 1 mm to about 5 mm.

10. The intraocular lens of claim 1, wherein said design wavelength is about 550 nm.

11. The intraocular lens of claim 1, wherein the optic exhibits a through-focus modulation transfer function that is asymmetric relative to a focal plane of said optic for at least a portion of a range of aperture sizes between about 1.5 mm to about 6 mm.

12. The intraocular lens of claim 1, wherein the effective optical power is characterized by a peak of a through-focus modulation transfer function of the optic at the design wavelength for an aperture size in a range between about 1.5 mm and 6 mm.

13. The ophthalmic lens of claim 12, wherein the depth of field is characterized as a full width at 15% contrast level in the through-focus modulation transfer function.

14. The ophthalmic lens of claim 1, wherein a difference of the effective power relative to the nominal optical power is between about 0.25 D and 1.75 D.

* * * * *